United States Patent
Righi et al.

[11] Patent Number: 5,163,918
[45] Date of Patent: Nov. 17, 1992

[54] DISPOSABLE SAFETY SYRINGE

[76] Inventors: Nardino Righi, Viale Lombardia 117 C/2, I-20093, Cologno Monzese; Roberto Rossi, Via Delle Ande 10, I-20151, Milano, both of Italy

[21] Appl. No.: 727,970

[22] Filed: Jul. 10, 1991

[30] Foreign Application Priority Data

Jul. 19, 1990 [IT] Italy ................. 20979 A/90
Jan. 9, 1991 [IT] Italy ............. GE91 A 000008

[51] Int. Cl.⁵ ........................................... A61M 5/32
[52] U.S. Cl. ............................... 604/198; 604/263; 604/110; 128/919
[58] Field of Search .......... 604/110, 111, 187, 192, 604/197, 198, 232, 263, 218

[56] References Cited

U.S. PATENT DOCUMENTS

| | | | |
|---|---|---|---|
| 4,639,249 | 1/1987 | Larson | 604/198 |
| 4,787,891 | 11/1988 | Levin et al. | 604/136 |
| 4,911,693 | 3/1990 | Paris | 604/192 |
| 4,927,416 | 5/1990 | Tomkiel | 604/198 |
| 4,932,947 | 6/1990 | Cardwell | 604/198 |
| 4,957,490 | 9/1990 | Byrne et al. | 604/197 |
| 5,013,301 | 5/1991 | Marotta et al. | 604/197 |
| 5,013,302 | 5/1991 | Schmidt | 604/198 |
| 5,061,251 | 10/1991 | Juhasz | 604/198 |
| 5,106,379 | 4/1992 | Leap | 604/198 |
| 5,114,404 | 5/1992 | Paxton et al. | 604/110 |
| 5,116,326 | 5/1992 | Schmidt | 604/198 |
| 5,120,309 | 6/1992 | Watts | 604/110 |
| 5,120,310 | 6/1992 | Shaw | 604/110 |
| 5,120,311 | 6/1992 | Sagstetter et al. | 604/110 |

FOREIGN PATENT DOCUMENTS

0273201 11/1989 Fed. Rep. of Germany ...... 604/187

*Primary Examiner*—C. Fred Rosenbaum
*Assistant Examiner*—Mark O. Polutta
*Attorney, Agent, or Firm*—Larson and Taylor

[57] ABSTRACT

A disposable safety syringe includes a barrel (1), an injection needle (4) fitted on the fore end of barrel (1), and a plunger (6) slidable in the barrel (1) from a syringe-filling utmost retracted position to a syringe emptying forwardmost position. The barrel is fitted with a manually driven stem (7) protruding from the rear end of barrel (1). A longitudinally slidable protective sleeve (12) is slidably fitted on the outside of barrel (1) so as to be movable from a retracted rest position in which the needle (4) is exposed into an advanced safety position in which the protective sleeve (12) extends around the needle (4) and entirely covers the same. A locking device (23, 25) is provided for automatically retaining in a not retractile manner the protective sleeve (12) to the barrel (1) in its advanced safety position.

20 Claims, 11 Drawing Sheets

DISPOSABLE SAFETY SYRINGE

SUMMARY OF THE INVENTION

The present invention relates to a disposable safety syringe which comprises a barrel, an injection needle fitted on the barrel fore end, and a plunger slidable in the barrel from a syringe-filling utmost retracted position to a syringe-emptying forwardmost position. The plunger is fitted with a manually driven stem protruding from the barrel rear end. A longitudinally slidable protective sleeve is slidably fitted on the outside of the barrel so as to be movable from a retracted rest position in which the needle is exposed to an advanced safety position in which the protective sleeve extends around the needle so as to entirely cover the same. A locking means is also provided for automatically retaining in a not retractile manner the protective sleeve to the barrel in its advanced safety position.

The object of the invention is to improve a syringe of the aforementioned type so as to better its operation, and to quite safely prevent the syringe from being re-used so as to eliminate any risk of infection originated from a re-using of the syringe. These objects are attained by utilizing simple and inexpensive means for the construction of the syringe which allows the production costs thereof to be kept at an extremely low value.

These aims are attained by the invention with the provision of a syringe of the type as described at the outset, characterized in that the protective sleeve lying in its retracted rest position is fastened to the barrel by clamping means engaged with a retaining rim on the rear end of the barrel. Further, the plunger stem is provided at its rear end section extending out of the barrel with releasing means for disengaging the clamping means from the retaining rim on the rear end of the barrel at the time when, on injecting, the forward stroke of the plunger is (or is almost) completed. The releasing means thus unfastens the protective sleeve from the barrel so that the protective sleeve is allowed to move into its advanced safety position.

Therefore, according to the invention, the protective sleeve lying in its retracted rest position is normally fastened to the syringe barrel by clamping means engaged with a retaining rim on the rear end of the barrel. In this condition of the protective sleeve, the needle is exposed and the syringe can be handled as usual, for example for being filled, with no risk of inadvertently displacing the protective sleeve. On injecting, at the end or a little before the end of the forward stroke of the plunger within the barrel, owing to a pressure being manually applied to the rear end of the plunger stem, the protective sleeve clamping means become automatically disengaged from the retaining rim on the barrel rear end by a releasing means provided on the rear end section of the plunger stem. This releasing means is configured for automatically disengaging the clamping means from the retaining rim. Thus, the protective sleeve is unfastened from the barrel and is allowed to move from its retracted rest position to its advanced safety position in which it covers the needle.

The protective sleeve, having been unfastened from the barrel, can then be moved manually by a user from its retracted rest position into its advanced safety position. Preferably, however, according to one preferred embodiment of the invention, a spring is fitted between the syringe barrel and the protective sleeve. This spring is loaded in the retracted rest position of the protective sleeve so that on the protective sleeve being unfastened from the barrel, this spring will automatically move the protective sleeve into its advanced safety position.

The clamping means carried by the protective sleeve and the releasing means carried by the plunger stem may be made in any suitable manner. According to a particularly simple and inexpensive embodiment, which however is very reliable, the clamping means are in the form of hook-like clamping teeth provided at the rear free ends of elastically flexible clamping tongues extending longitudinally of the protective sleeve and are made of one piece therewith. The clamping tongues are also formed with slanted abutment faces for cooperating with respective actuating surfaces of a pusher member secured to the rear end section of the plunger stem. The whole arrangement is such that, on injecting, the actuating surfaces of the pusher member will be caused to act at the end or almost at the end of the plunger forward stroke upon the slanted abutment faces of the clamping tongues. Thus, these tongues will be elastically flexed from a clamping position in which their hook-like teeth are engaged with the retaining rim on the rear end of the barrel to a releasing position in which their hook-like teeth are disengaged from the retaining rim.

According to one preferred embodiment of the invention, by which the use of the syringe is made very comfortable, the protective sleeve lying in its retracted rest position axially abuts backward against at least one stop member provided at the rear end of the barrel. At its rear end, the protective sleeve is formed with at least two diametrically opposite tabs radially extending from the periphery thereof. These tabs are sustained in place by two fingers of a user's hand holding the syringe at the time of an injection. Thus, when an injection is terminated and because the protective sleeve had been unfastened from the barrel by the releasing means provided on the plunger stem, the protective sleeve will be moved forward on the syringe barrel due to the bias of the spring only when the protective sleeve rear tabs are released by the user's fingers.

According to another advantageous embodiment of the invention, the syringe needle is attached to a needle-carrying member removably fitted in and/or on the barrel fore end. Then, the locking means for automatically retaining to the barrel the protective sleeve in its advanced safety position is engaged with the needle-carrying member. The locking means preferably consists of at least one locking inward projection provided in the protective sleeve for cooperating with a respective outward projection in the needle-carrying member, and of at least one locking tongue formed in the protective sleeve by means of cuts made therein and extending in the longitudinal direction thereof. The forward end of the locking tongue is integral with the protective sleeve, and the free rear end thereof tends to elastically flex radially inwardly. This locking tongue cooperates with a respective outward projection in the needle-carrying member. The whole arrangement is such that with the protective sleeve lying in its advanced safety position, the locking inward projection in the protective sleeve bears forwardly against the respective outward projection in the needle-carrying member, and the free rear end of the locking tongue bears backwardly against the respective outward projection in the needle-carrying member.

In this embodiment, the protective sleeve is locked in its advanced safety position in both directions, i.e., either forward and backward. However, the protective sleeve is not directly locked to the syringe barrel, but instead is locked to the needle-carrying member removably fitted in or on the barrel fore end so that the needle-carrying member is unremovably secured to the protective sleeve. Therefore, when a person attempting to re-use the syringe succeeds in slipping the protective sleeve off barrel, for example in the forward direction, the needle-carrying member and the needle will also be detached from the barrel along with the protective sleeve and will be firmly held and confined inside the protective sleeve.

Other embodiments of the invention are characterized hereinafter, and the advantages attained thereby will become clearly apparent from the following disclosure of some embodiments shown in the accompanying drawings.

BRIEF DESCRIPTION OF THE DRAWINGS

FIG. 6 is a perspective view showing the manner of holding the syringe of FIGS. 1 to 5 at the time of an injection.

DESCRIPTION OF THE PREFERRED EMBODIMENTS

In the following disclosure and in the attached Claims, the expression "syringe fore end" is meant to refer to the end of the syringe that is fitted with the injection needle and the rear end of the syringe is the end thereof lying opposite to the needle. Also, all of the syringe members, but for the needle, are preferably made from a suitable plastics material or the like, unless it is differently specified.

Referring to the embodiment shown in FIGS. 1 to 7, the disposable safety syringe comprises a barrel 1 with a conical forward end 2 on which the needle-carrying member 3 is fitted. The needle-carrying member 3 is held on forward end 2 by friction by means of a matching conical hole formed at the rear end thereof, the rear end of needle 4 being firmly incorporated in the hole. The needle 4 is normally protected by a needle-covering cap 5 removably fitted on the fore end of the needle-carrying member 3 so as to be caused to abut against an undercut 103 provided therein. In barrel 1, a plunger 6 is axially slidable in a fluid-tight manner and the head 8 of a manually driven stem 7 is engaged in the plunger 6. The rear end section of stem 7 extends backwardly out of barrel 1 and is provided with a knob 9 on the rear end thereof. Preferably, the stem 7 has in cross section a non-circular shape, and is for example, T-like or X-like shaped. The rear end portion of barrel 1 is so enlarged that a substantially cylindrical boxlike head 10 is formed which is provided with two diametrically opposite tabs 11 radially extending from its periphery.

Figure 1:
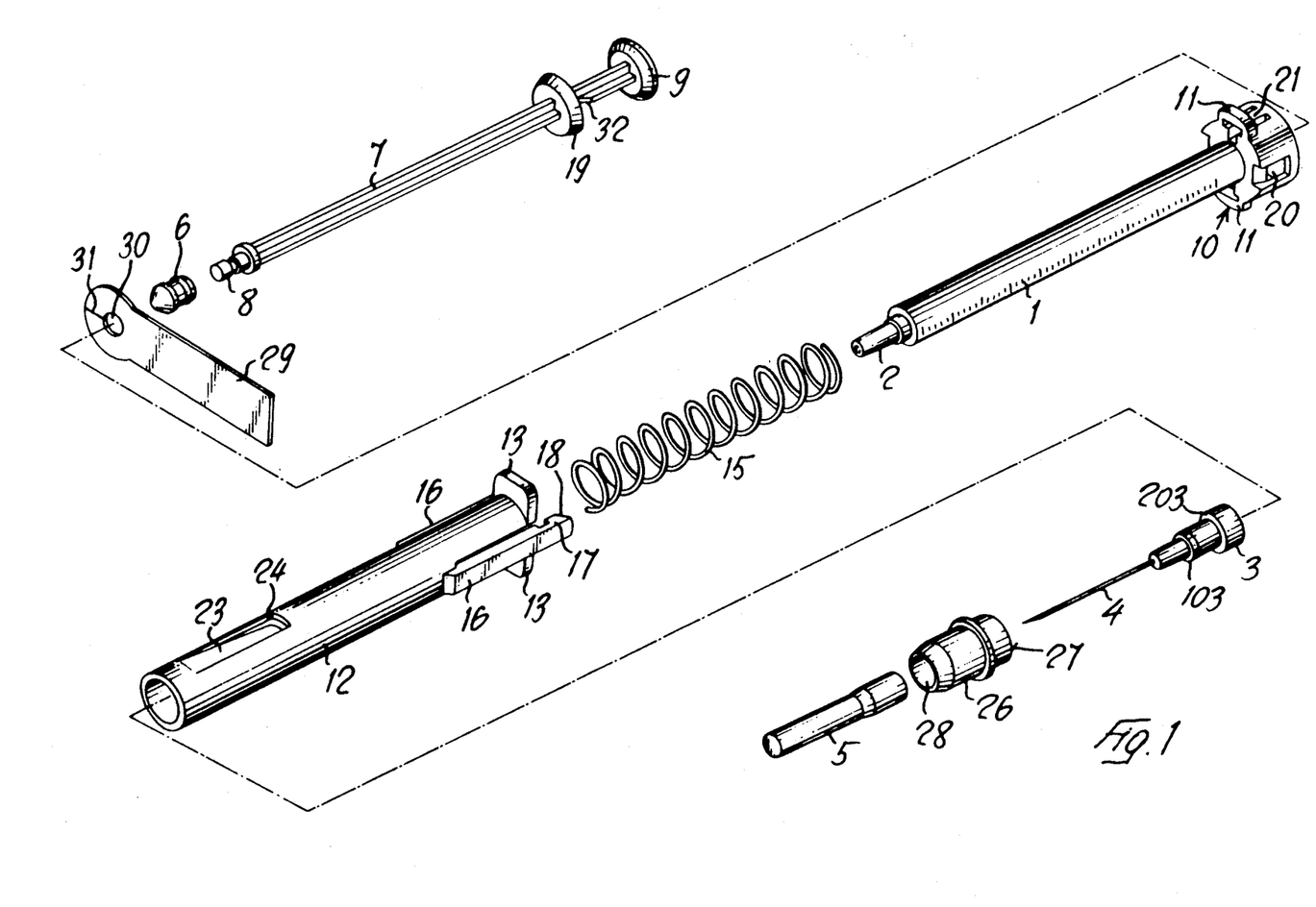
FIG. 1 is an exploded perspective view of a first embodiment of the syringe according to the invention.
Figure 2:
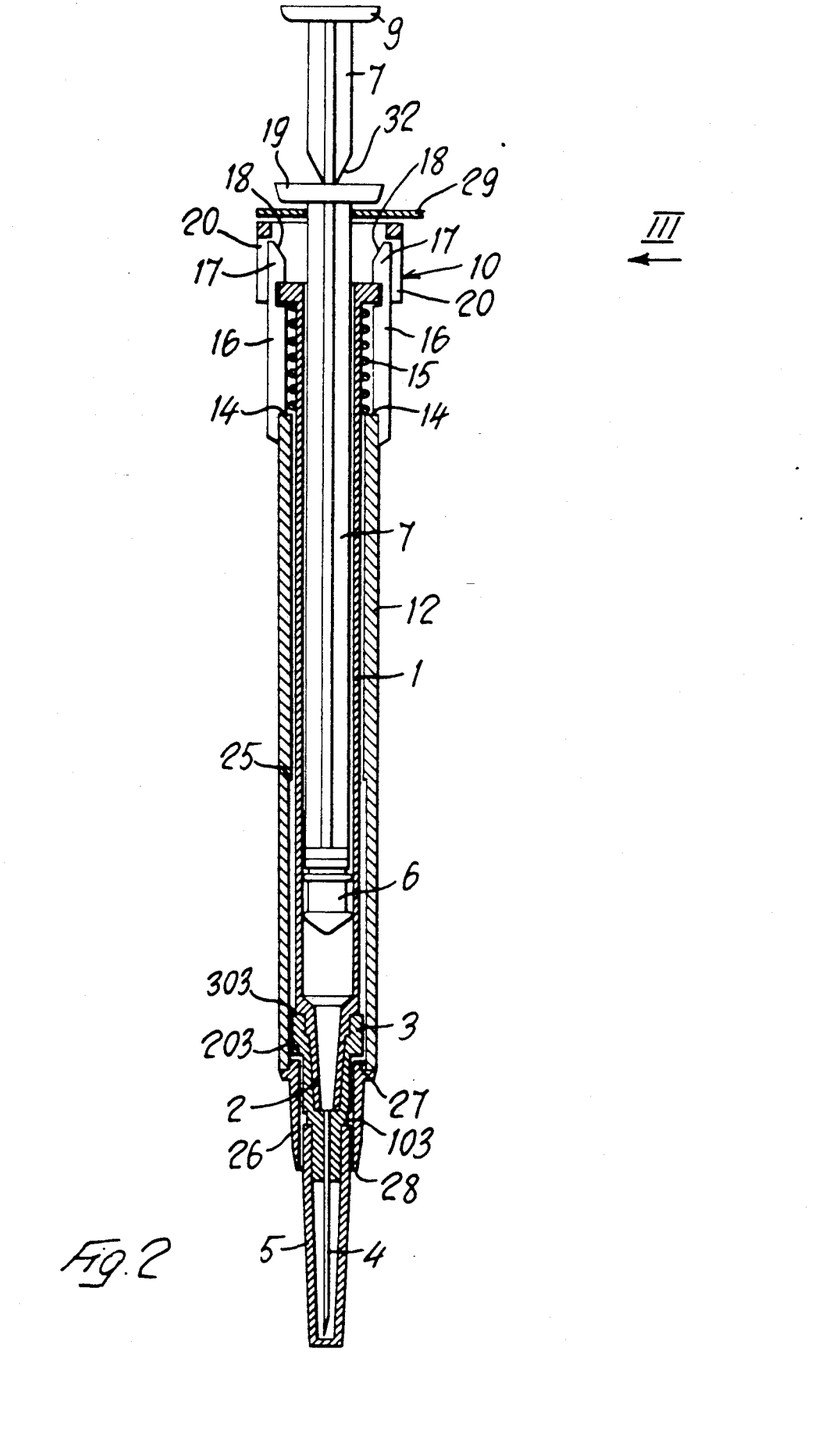
FIG. 2 is a longitudinal sectional view of the syringe according to FIG. 1, with the protective sleeve lying in its retracted position.
Figure 3:
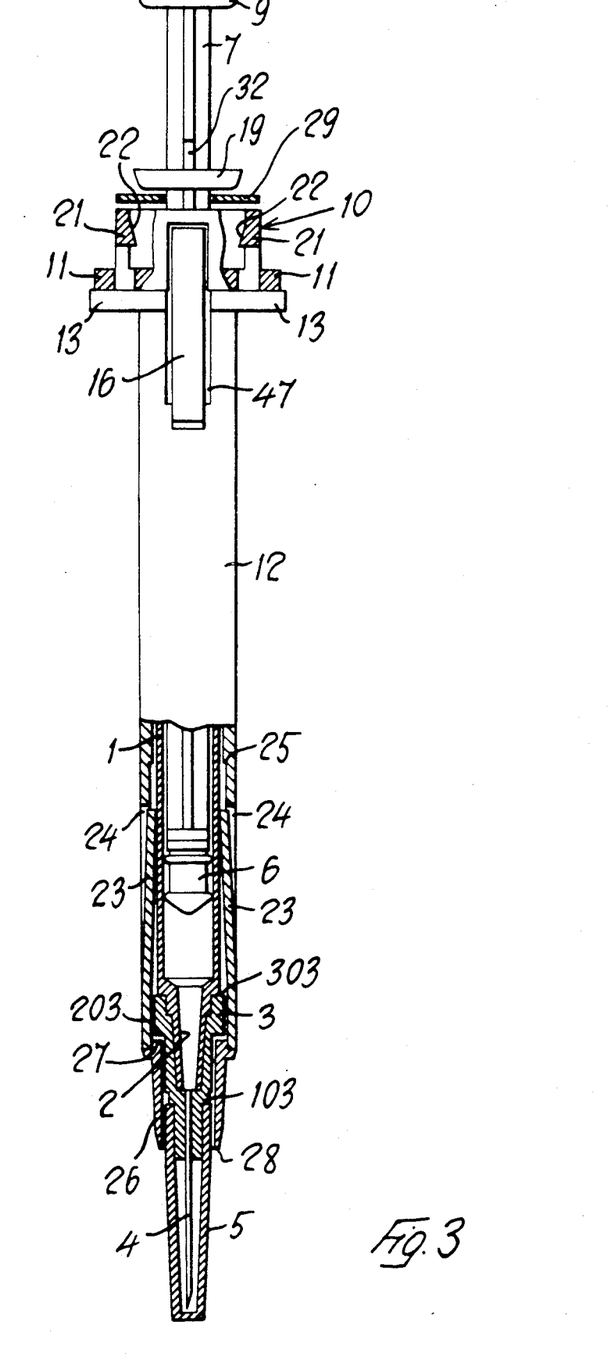
FIG. 3 shows the syringe according to FIG. 2 viewed in the direction of arrow III in this latter Figure, and with some parts in section.

A protective sleeve 12 is fitted on the outside of barrel 1 so as to be longitudinally slidably thereon. The rear end of the protective sleeve 12 is formed with two diametrically opposite tabs 13 which extend radially from the periphery thereof and are like the tabs 11 of barrel 1. A helical spiral spring 15 of metal is interposed between an inward step 14, provided in the protective sleeve 12 at a distance from its rear end, and the boxlike head 10 of barrel 1.

The protective sleeve 12 is provided at its rear end with two clamping tongues 16 which are made of one piece therewith and which are formed therein at two diametrically opposite locations. Each clamping tongue 16 extends lengthwise of the protective sleeve 12 at a longitudinal aperture 47 made therein. The forward end of the clamping tongue 16, i.e., the end thereof which is turned toward the needle 4, is integral with the protective sleeve 12. The rear end of clamping tongue 16 extends beyond the rear end of the protective sleeve 12 and protrudes from the rear end thereof. Each clamping tongue 16 can be elastically flexed outwardly in the radial direction, and at its rear end is formed with a hook-like clamping tooth 17 which is turned radially inwardly. Each clamping tongue 16 is further provided at the rear end of its clamping tooth 17 with a slanted abutment face 18 which is downwardly inwardly inclined. Abutment faces 18 cooperate with the correspondingly inclined peripheral edge of a disc-shaped pusher member 19 secured to the stem 7 of plunger 6 close to the rear side of the boxlike head 10 of barrel 1, which pusher member 19 is opposite to and designed to go inbetween the clamping tongues 16.

The boxlike head 10 at the rear end of barrel 1 is formed close to each clamping tongue 16 with an aperture 20 extending into the bottom and into the sidewall of the boxlike head 10. Thus, each clamping tongue 16 is allowed to penetrate into the boxlike head 10 and to be engaged by its hook-like clamping tooth 17 with the bottom of the head 10. By means of cuts made in the sidewall of the boxlike head 10 at the rear end of barrel 1, two diametrically opposite slip-back preventing teeth 21 are formed which are angularly offset by 90° from the two apertures 20 for the clamping tongues 16. The slip-back preventing teeth 21 can be caused to elastically diverge radially outwardly from each other, and have their facing inward sides formed with slanted abutment faces 22 which are downwardly inwardly inclined. The slanted abutment faces 22 cooperate with the correspondingly inclined peripheral edge of the disc-shaped pusher member 19.

In the fore part of the protective sleeve 12 two diametrically opposite locking tongues 23 are provided which are formed in the protective sleeve 12 by means of cuts 24 made therein. Each locking tongue 23 extends in the longitudinal direction of the protective sleeve 12. The forward end of each locking tongue 23 is integral with the protective sleeve 12, and the rear end thereof is loose and tends to elastically flex radially inwardly. The rear free ends of the locking tongues 23 cooperate with a peripheral outward undercut 203 in the needle-carrying member 3. The protective sleeve 12 is formed in the direction of the syringe rear end, at a distance from the locking tongues 23, with a locking inward projection 25. Locking inward projection 25 may be made in the form of an annular undercut or may consist of the fore ends of a plurality of ribs (not shown) provided at the interior of the protective sleeve 12. The locking inward projection 25 in the protective sleeve 12 cooperates with the annular edge portion 303 of the rear end rim of the needle-carrying member 3. The needle-carrying member 3, having been fitted into position on the fore end 2 of barrel 1, actually protrudes from the periphery of barrel 1 by the edge portion of its rear end rim so that an outward annular step 303 is formed which is associated with the locking inward projection 25 in the protective sleeve 12.

A tubular member 26 is engaged in the fore end of the protective sleeve 12 and is fastened thereto such as by gluing or by welding. The rear end rim of the tubular member 26 forms a retaining inward annular projection 27 in the protective sleeve 12. Front hole 28 in tubular member 26 is tapered relative to the inside diameter of the protective sleeve 12, and is only slightly greater than the outside diameter of the rear end portion of the needle-covering cap 5.

The syringe is sold to a user in the condition shown in FIGS. 2 and 3, with the plunger 6 slightly drawn back from its forwardmost position and with the syringe entirely emptied. In this condition of the syringe, the disc-shaped pusher member 19 is a little outside of the boxlike head 10 at the rear end of barrel 1 and is prevented from getting into the head by a tearable safety strip 29 of paper, paperboard, or the like. Through a hole 30 and a radial cut 31, the strip 29 is threaded on the stem 7 of plunger 6 and is positioned between the disc-shaped pusher member 19 and the rim of the opening at the rear side of the boxlike head 10. The protective sleeve 12 lies in its retracted rest position in which the clamping tongues 16 are caused to penetrate through the apertures 20 into the boxlike head 10 of barrel 1. Thus, the hook-like clamping teeth 17 of the clamping tongues 16 are engaged with the bottom of the head 10 whereby the protective sleeve 12 is fastened to the barrel 1.

With the protective sleeve 12 lying in its retracted rest position, the spring 15 is loaded (compressed) and the tabs 13 radially extending from the periphery of the protective sleeve 12 are caused to bear, or almost bear, against the forward face of the corresponding tabs 11 provided on the boxlike head 10 of barrel 1. Moreover, when the protective sleeve 12 is in its retracted rest position, the tapered fore part 26 thereof extends substantially to the forward end of the needle-carrying member 3 so that the needle 4 is set free in an exposed condition at the time when the needle-covering cap 5 will be forwardly disengaged. Concurrently, the protective sleeve 12 is caused to bear, or almost bear, by its inward annular projection 27 formed by the rear end rim of the tubular member 26 backwardly against the outward annular undercut 203 in the needle-carrying member 3. In the above-disclosed condition of the syringe according to FIGS. 2 and 3, the plunger 6 can be freely retracted by drawing back its stem 7 so that the syringe barrel 1 will be filled as usual by sucking the to-be-injected liquid through the exposed needle 4.

To be allowed to make an injection, the safety strip 29 has to be torn away, and the syringe has to be held as shown in FIG. 6. As shown, the syringe is held with two fingers of a user's hand resting each on the front side of the respective tab 13 radially extending from the periphery of the protective sleeve 12 rear end, and with the user's thumb placed on the knob 9 of the plunger stem 7 pressing forward the plunger 6. Toward the end of the forward stroke of the plunger 6, the disc-shaped pusher member 19 is caused to penetrate into the barrel 1 boxlike head 10 from the opening at the rear end thereof and by its peripheral edge is caused to act on the slanted abutment faces 18 of the clamping tongues 16. Therefore, the clamping tongues 16 are caused to elastically diverge outwardly from each other so that their hook-like clamping teeth 17 become disengaged from the bottom of the boxlike head 10 of barrel 1. The protective sleeve 12 is thus unfastened from barrel 1, but is still retained in its retracted rest position against the load of the pressure spring 15 by the user's hand, as disclosed by referring to FIG. 6.

Before and/or as the clamping tongues 16 are opened out as disclosed above, the disc-shaped pusher member 19 is also caused to act by its peripheral edge also upon the slanted abutment faces 22 of the slip-back preventing teeth 21 and to pass thereover. The teeth 21 are thus elastically opened out, so that they are caused to snappingly engage the top side of the disc-shaped pusher member 19. Therefore, on injecting, the pusher member 19 is locked in the boxlike head 10 of barrel 1 at the end or almost at the end of the forward stroke of plunger 6 between the bottom of the head 10 and the slip-back preventing teeth 21. In such a position, the clamping tongues 16 are kept in their opened out condition and the protective sleeve 12 is thus disengaged from the barrel 1, as shown in the upper part of FIG. 4.

Figure 4:
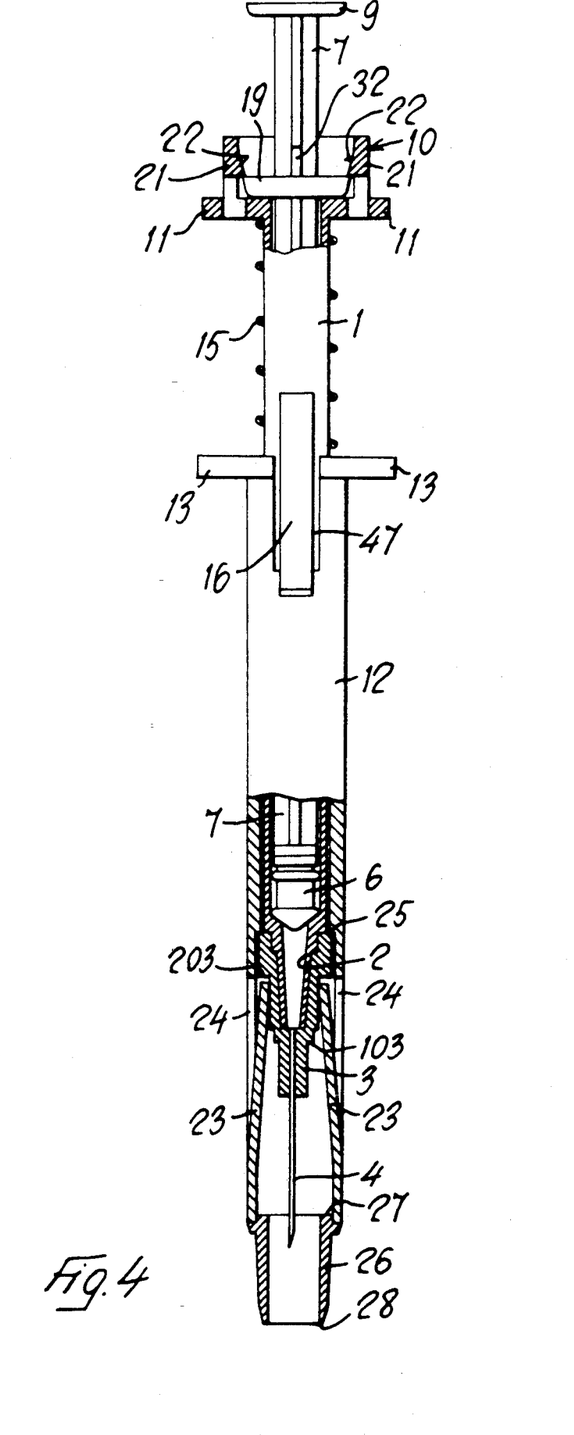
FIG. 4 is a same view of the syringe as in FIG. 3, however with the protective sleeve lying in its advanced safety position.

Once the injection has been made, the peripheral radial tabs 13 extending from the rear end of the protective sleeve 12 are released by the user so that the protective sleeve which is now disengaged from the barrel 1 is moved forward by the spring 15, either gradually or snappingly into its advanced safety position shown in FIG. 4. The protective sleeve lying in its advanced safety position extends around the needle 4 so as to entirely cover the same. The protective sleeve 12 is at the same time caused to abut by its locking inward projection 25 backward against the annular step 303 formed by the edge portion of the rear end rim of the needle-carrying member 3, and the rear free ends of the locking tongues 23 are simultaneously caused to bear backward against the outward annular undercut 203 in the needle-carrying member 3, as more particularly shown in FIG. 7. Thus, the protective sleeve lying in its advanced safety position is unremovably locked to the barrel in both senses of its longitudinal direction, i.e., either forward and backward, by means of the needle-carrying member 3.

Figure 5:
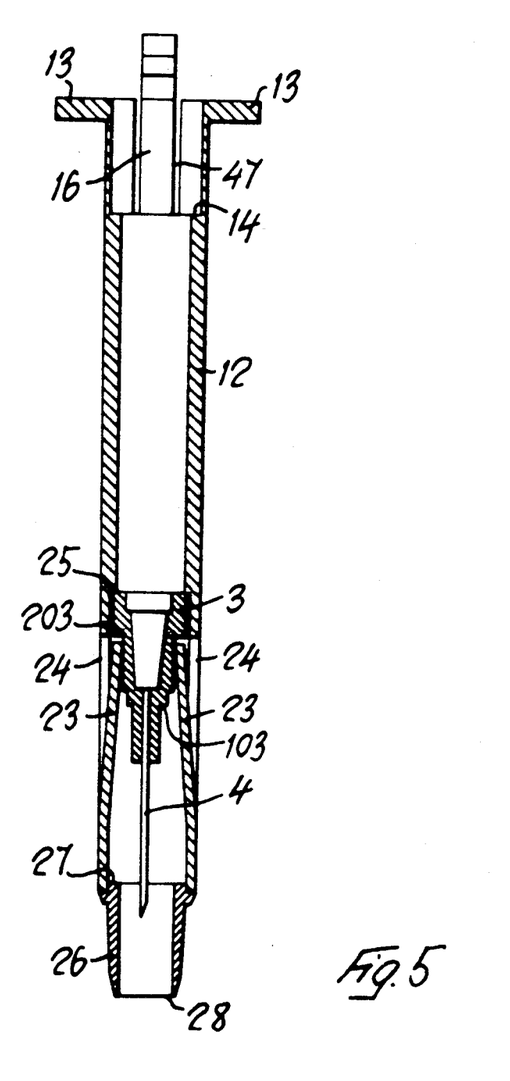
FIG. 5 is a longitudinal sectional view of the syringe with the protective sleeve having been separated from the syringe along with the needle-carrying member and the needle, as a result of an attempt to re-use the syringe.
Figure 7:
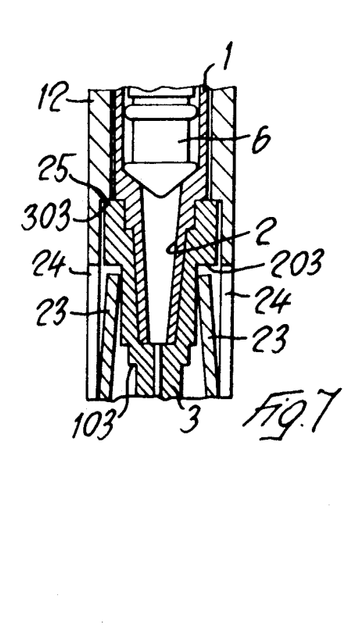
FIG. 7 is a longitudinal sectional view in an enlarged scale showing a detail of the syringe according to FIG. 4.

Should a person attempt to slip the protective sleeve 12 forwardly off the barrel 1 when trying to re-use the syringe, the needle-carrying member 3 would be, at the most, disengaged from the conical forward end of barrel 1. Thus, the protective sleeve 12 would be detached from barrel 1 together with the needle-carrying member 3 that is inseparably shut in the protective sleeve 12, and so together with the needle 4 enclosed in the protective sleeve 12, as shown in FIG. 5. The protective sleeve 12 can be made with no problem and at a low cost from such a tough and strong plastics material that the protective sleeve could not be broken without damaging and rendering the needle-carrying member 3 and also the needle 4 unusable. Moreover, the fore part 26 of the protective sleeve 12 has such a narrow hole 28 and extends over such a long section beyond the pointed end of needle 4 that the finger of a person is prevented from reaching to the needle 4 from the fore end of the syringe.

The stem 7 of plunger 6 may be provided with an easily breakable weakened portion 32 at a point between the disc shaped pusher member 19 and the knob 9 on the rear end of stem 7, preferably at a point being adjacent to the disc-shaped pusher member 19. Owing to the provision of this weakened portion, the rear end section of stem 7 will be broken when an attempt is made to pull back the plunger 6 for trying to re-use the syringe once the disc-shaped pusher member 19 has been locked in the boxlike head 10 of barred 1 by the slip-back preventing teeth 21.

The protective sleeve 12 can be slidably but non-rotatably fitted on the barrel 1 with the aid of simple means known to those skilled in the art, such as by an inward projection in sleeve 12 slidably engaged in a longitudinal groove in the outward side of barrel 1, or vice-versa.

Figure 8:
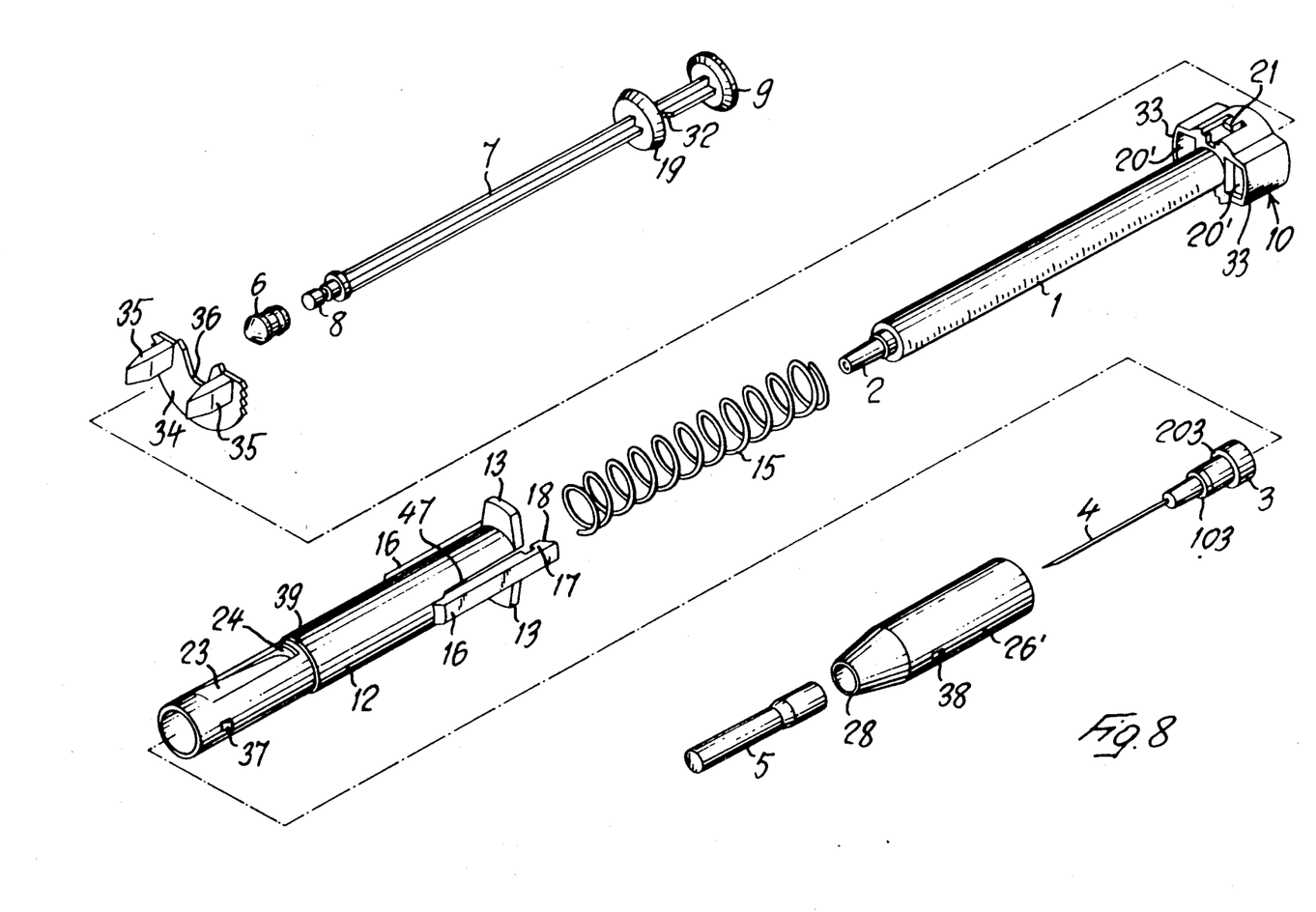
FIG. 8 is an exploded perspective view showing a second embodiment of the syringe according to the invention.
Figure 9:
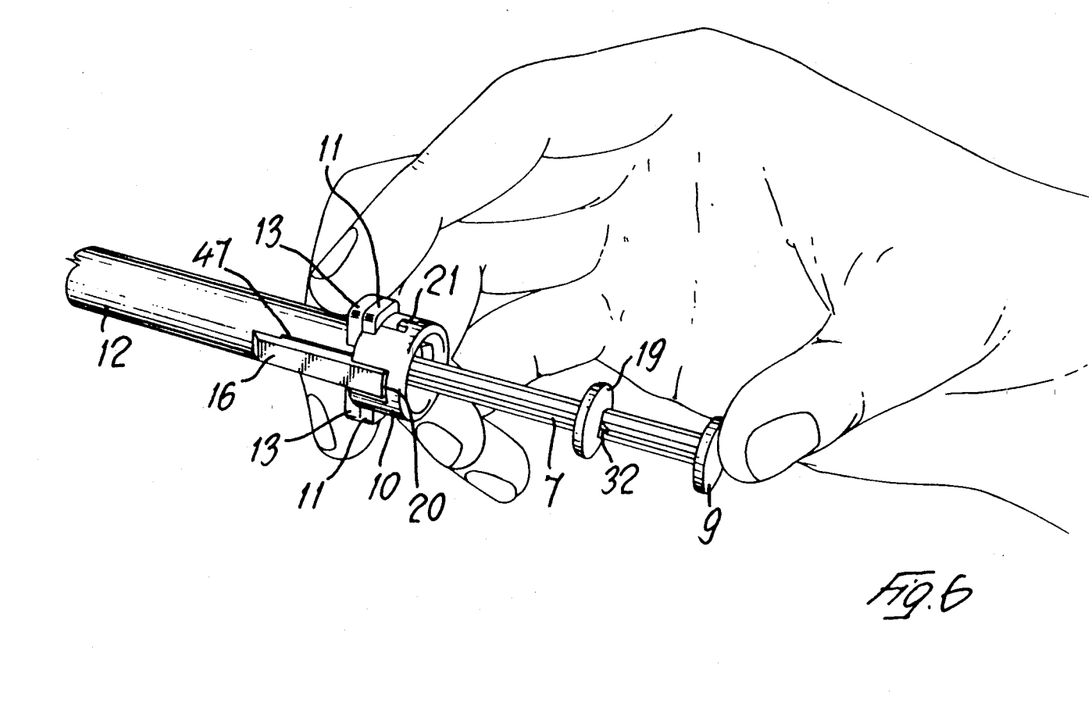
FIG. 9 is a longitudinal sectional view in an enlarged scale showing the rear end of the syringe according to FIG. 8 with the protective sleeve lying in its retracted rest position.
Figure 10:
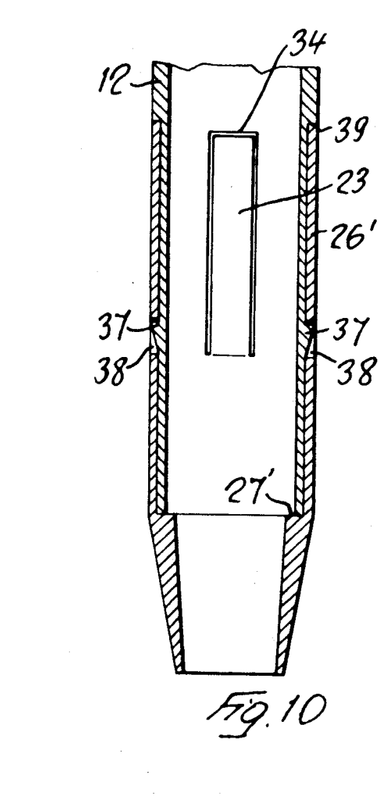
FIG. 10 is a longitudinal sectional view in the same scale as in FIG. 9 showing the fore end of the protective sleeve of the syringe according to FIG. 8.

The embodiment of the syringe according to FIGS. 8, 9, and 10 substantially corresponds to the embodiment as disclosed above by referring to the FIGS. 1 to 7, like parts being designated by the same reference numerals. However, in the modified embodiment according to FIGS. 8 to 10, the boxlike head 10 at the rear end of barrel 1 has a sidewall 33. The sidewall 33 radially covers from the outside the rear free ends forming the hook-like clamping teeth 17 of the clamping tongues 16, which enter into the boxlike head 10 through the apertures 20' in the bottom thereof.

In this embodiment, the removable safety means for initially preventing the disc-shaped pusher member 19 from getting into the boxlike head 10 at the rear end of barrel 1 consist of a substantially part-circular small cover member 34 formed with a central opening 36 for allowing the stem 7 to pass therethrough. The cover member 34 is provided in place of the tearable strip 29 of paper or paperboard. The small cover member 34 is applied to the opening at the rear side of the boxlike head 10 and, for this purpose, is formed at its front side which is turned toward the syringe fore end with two diametrically opposite wedge-shaped teeth 35. The teeth 35 extend from the cover member 34 and are introduced into the opening at the rear side of the boxlike head 10 so as to be inserted respectively between the two clamping tongues 16 and the sidewall 33. Thus, by means of their hook-like clamping teeth 17, clamping tongues 16 are engaged with the bottom of the boxlike head 10 and the respective portion of the sidewall 33 thereof, as shown in FIG. 9. Thus, the two teeth 35 will hold the cover member 34 in position on the boxlike head 10 at the rear end of barrel 1, and at the same time will prevent the rear free ends of the clamping tongues 16 from being radially outwardly flexed and then from being disengaged from the boxlike head 10. The thus applied cover member 34 partly closes the opening of the boxlike head 10 at the rear end of barrel 1, and therefore prevents the disc-shaped pusher member 19 from entering into the head 10.

Before the syringe is used for an injection, the cover member 34 must be removed. Therefore, a syringe user has to grip the cover member 34 with two fingers of his hand close to the preferably indented peripheral edge thereof at two diametrically opposite positions. Then, the user axially disengages the cover member 34 from the boxlike head 10 at the rear end of barrel 1, and finally slips the same radially off the stem 7 of plunger 6.

According to the embodiment shown in FIGS. 8, 9, and 10, the tubular member 26' forming the fore part of the protective sleeve 12 has a tapered front hole 28 which is only a little wider than the rear end portion of the needle-covering cap 5. The tubular member 26' is threaded on the outside of the protective sleeve 12 and is snappingly engaged therewith in an unremovable manner. Therefore, the protective sleeve 12 is provided with a front end section of a reduced diameter in which the locking tongues 23 are formed, and on which the tubular member 26' is fitted so as to be caused to abut against an outward annular undercut 39 formed in the protective sleeve 12.

The tubular member 26' is locked in this position by two outward detents 37 which are provided in diametrically opposite positions on the outside of the protective sleeve 12 and which are snappingly engaged into respective peripheral slots 38 in the tubular member 26'. With the tubular member 26' being in its engaged position, the tubular member is caused to abut by an inward annular step 27' thereof against the fore end rim of the protective sleeve 12, as more particularly shown in FIG. 10. The width of the internal annular step 27' is such that this step partly extends also into the protective sleeve 12, so that its radially inwardly edge portion forms the retaining annular projection which is for cooperating with the outward annular undercut 203 in the needle-carrying member 3.

Figure 16:
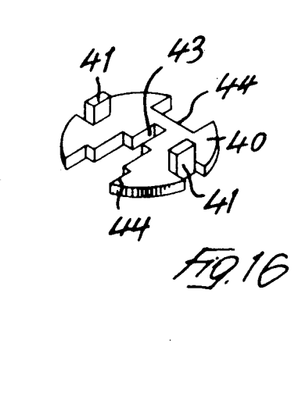

In FIGS. 11 to 16 showing a further modified embodiment of the syringe according to the invention, the already described parts are also designated by the same reference numerals. In this embodiment, a platelet 40 which is shown in upturned position in FIG. 16 is arranged on the bottom of the boxlike head 10 of barrel 1. By means of two diametrically opposite tongues 41, the platelet 40 is engaged in the respective apertures 42 formed in the bottom of the head 10. The platelet 40 is thus non-rotatably retained in the boxlike head 10 of barrel 1, and is caused to non-rotatably guide the stem 7 of plunger 6. The stem 7 is T-shaped in cross section, and by the leg of its T-shaped cross section is passed through a relative narrow opening 43 in platelet 40.

Instead of two diametrically opposite clamping tongues 16 as provided in the embodiments shown in FIGS. 1 to 10, two pairs of diametrically opposite clamping tongues 16' are provided in the syringe according to the modified embodiment shown in FIGS. 11 to 16 at respective longitudinal apertures 47 in the protective sleeve 12. The two clamping tongues 16' of each pair are arranged in facing relation along an arc and in a substantially tangential plane with their hook-like clamping teeth 17' being turned outwardly in opposite directions and with their slanted abutment faces 18' being downwardly outwardly inclined. Each pair of clamping tongues 16' is caused to get into the boxlike head 10 at the rear end of barrel 1 through an aperture 20' in the bottom of the head 10 and through a relative peripheral aperture 44 formed in platelet 40. The hook-like clamping teeth 17' of the clamping tongues 16' are each engaged with the edges of the relative peripheral aperture 44 in platelet 40. In register with each pair of clamping tongues 16' the disc-shaped pusher member 19' secured to the stem 7 of plunger 6 is formed with an opening consisting of a peripheral recess 45.

On injecting, the free ends of the pairs of clamping tongues 16' come to be inserted at the end, or almost at the end, of the forward stroke of plunger 6 into the peripheral recesses 45 in the disc-shaped pusher member 19' which cooperate with the slanted abutment faces 18' of the pairs of clamping tongues 16'. Consequently, disc-shaped member 19' elastically draws the two clamping tongues 16' of each pair near to each other, as more particularly shown in FIG. 13. Then, the hook-like clamping teeth 17' of the clamping tongues 16' become disengaged from the edges of the respective peripheral aperture 44 in platelet 40 on the bottom of the boxlike head 10 at the rear end of barrel 1 so that the protective sleeve 12 is unfastened from the barrel 1 and is moved forward by the bias of spring 15, as disclosed above by referring to FIGS. 1 to 7.

Figure 11:
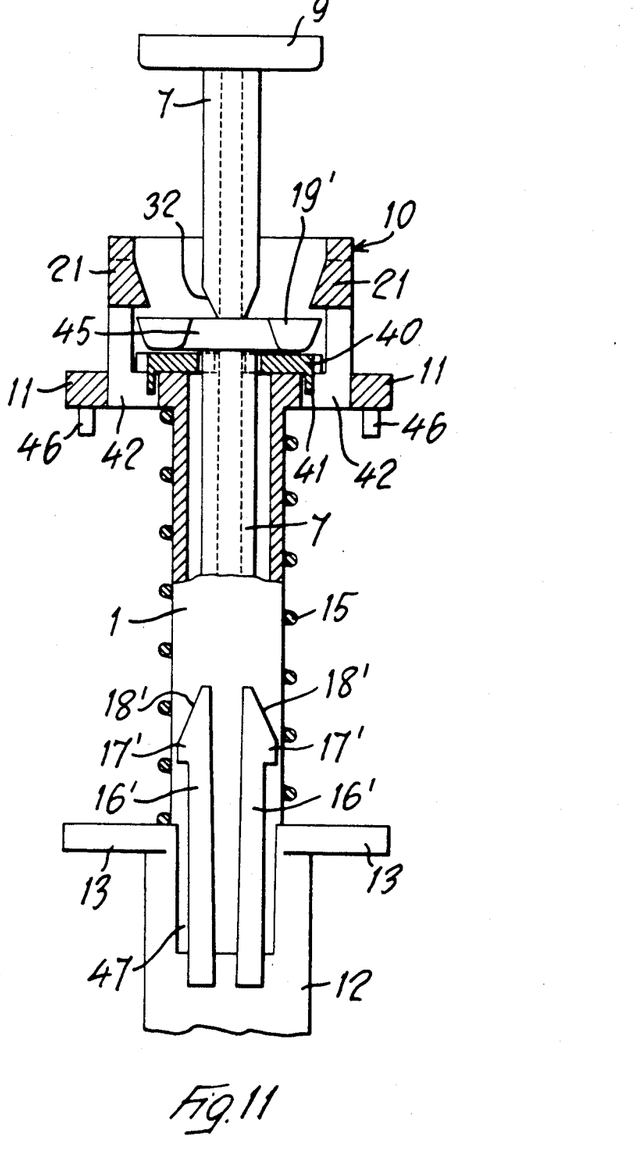
FIG. 11 is a view with parts in section showing the rear end of the syringe according to a third embodiment of the invention, with the protective sleeve lying in its advanced safety position.
Figure 12:
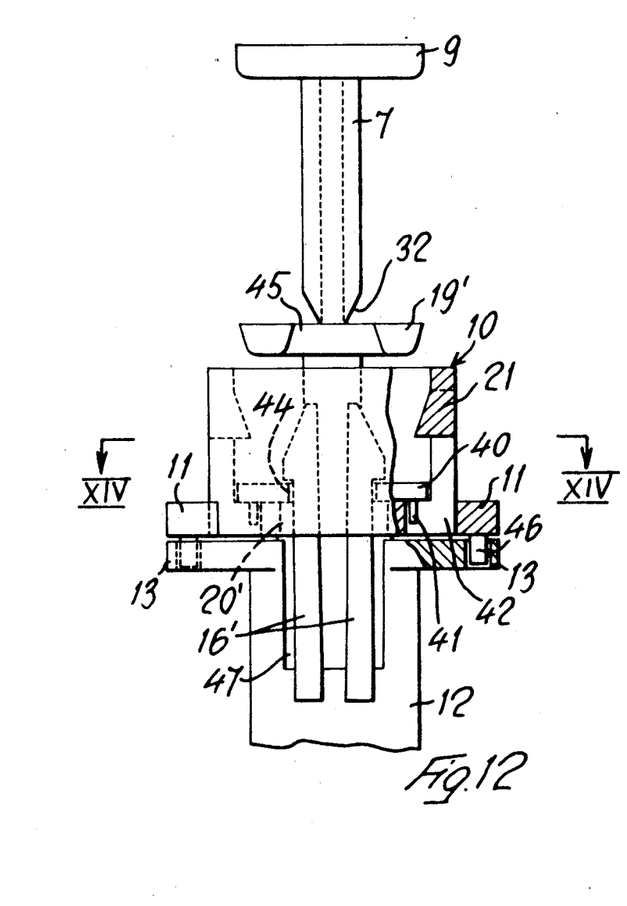
FIGS. 12 and 13 are elevational part-sectional views showing the rear end of the syringe according to FIG. 11, with the protective sleeve in its retracted rest position in FIG. 12 and at the time when the sleeve is being released from the syringe barrel in FIG. 13.
Figure 13:
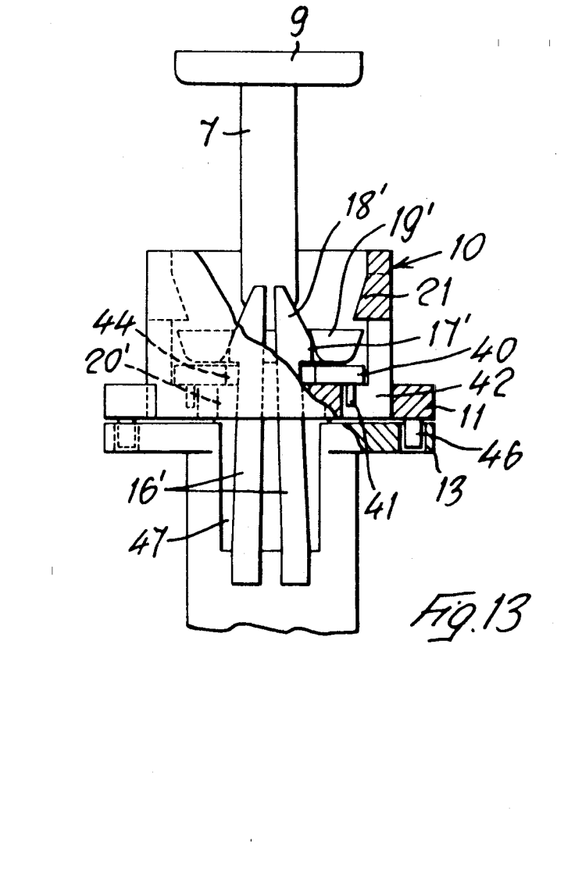
Figure 14:
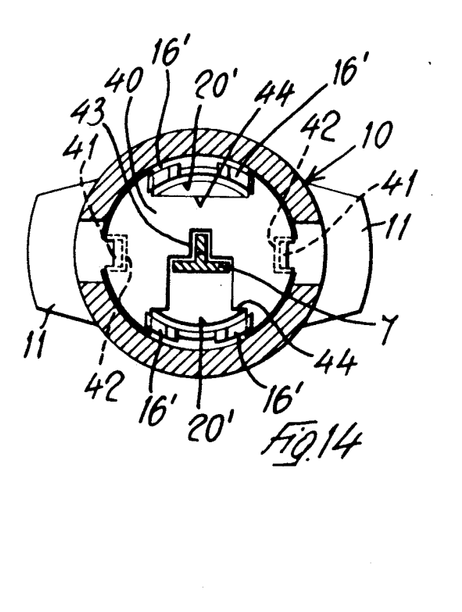
FIG. 14 is a cross-sectional view taken on line XIV—XIV in FIG. 12.
Figure 15:
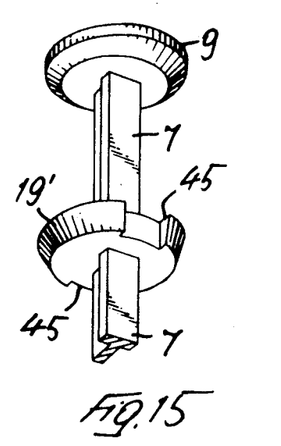
FIGS. 15 and 16 are perspective views showing two details of the syringe according to FIGS. 11 to 14.

At the time when the injection is terminated, the disc-shaped pusher member 19' becomes locked between the platelet 40 and the slip-back preventing teeth 21 provided in the boxlike head 10, as more particularly shown in FIG. 11. The diametrically opposite tabs 11 radially extending from the periphery of the boxlike head 10 are preferably fitted with pins 46 which are engaged in respective holes in tabs 13 radially extending from the periphery of the protective sleeve 12.

We claim:
1. A disposable safety syringe comprising:
   a barrel having a fore end, a rear end, and a retaining rim at the rear end;
   an injection needle fitted on the fore end of said barrel;
   a plunger which is slidable in said barrel from a syringe-filling utmost retracted position to a syringe-emptying forwardmost position;
   a stem which is fitted to said plunger for manually moving said plunger between the retracted and forwardmost positions, said stem including a rear end section protruding from the rear end of said barrel;
   a longitudinally slidable protective sleeve slidably fitted about said barrel which is movable from an initial retracted rest position in which said needle is exposed to an advanced safety position in which said needle is surrounded thereby so that said protective sleeve covers said needle;
   a clamping means for fastening said protective sleeve in the initial retracted position to said retaining rim of said barrel;
   a releasing means provided at said rear end section of said stem for disengaging said clamping means from said retaining rim when said plunger is manually driven by said stem at least almost to the forwardmost position such that said protective sleeve is movable to the advanced safety position; and
   a locking means for locking said protective sleeve in the advanced safety position after movement from the retracted rest position.

2. A safety syringe as claimed in claim 1 and further including a spring fitted between said barrel and said protective sleeve which is loaded to automatically move said protective sleeve toward the advance safety position from the retracted rest position when said releasing means disengages said clamping means.

3. A safety syringe as claimed in claim 1 wherein said clamping means is two elastically flexible clamping tongues each formed in one piece with said protective sleeve and extending in a longitudinal direction thereof, each said clamping tongue including a rear free end and a hook-like clamping tooth at the free end which engages said retaining rim of said barrel when said protective sleeve is in the retracted rest position and which includes an abutment face; and wherein said releasing means includes a disc-shaped pusher member secured to the rear end section of said stem having actuating surfaces for cooperating with said abutment faces of said clamping teeth such that as said plunger is moved at least almost to the forwardmost position said actuating surfaces of said pusher member engage said slanted abutment faces of said clamping teeth to elastically flex said hook-like clamping teeth from engagement with said retaining rim.

4. A sefety syringe as claimed in claim 3 wherein said clamping tongues are provided on diametrically opposite sides of said protective sleeve and respective said slanted abutment faces are turned toward one another such that said tongues are elastically moved radially from a longitudinal axis of said barrel as said disc-shaped pusher member is axially received between said slanted abutment faces.

5. A safety syringe as claimed in claim 3 wherein there are two pairs of said clamping tongues, said clamping tongues of each pair being diametrically opposite one another and having said slanted abutment faces of said clamping teeth turned outwardly of each other in opposite directions and drawable near to each other from a clamping position of said clamping teeth into a releasing position of said clamping teeth; and wherein said disc-shaped pusher member includes a recess for each said pair of said clamping teeth into which respective said pairs of said clamping teeth are axially received to flex said clamping teeth from engagement with said retaining rim.

6. A safety syringe as claimed in claim 3 wherein said rear end of said barrel includes two diametrically opposite slip-back preventing teeth which are elastically divergeable radially outward from one another, said slip-back preventing teeth including facing inward sides formed with slanted abutment faces such that said slanted abutment faces are engaged by said pusher member of said stem and pushed elastically outward as said pusher member passes therebetween and such that after passage said slip-back preventing teeth engage a rear side of said pusher member to lock said pusher member together with said stem in the forwardmost position of said plunger and thereby to prevent any backward displacement of said pusher member and said stem.

7. A safety syringe as claimed in claim 6 wherein said rear end of said barrel includes a box-like head which is integrally formed therewith, said box-like head including (a) sidewalls and cuts in associated said sidewalls which form said slip-back preventing teeth, (b) apertures formed in a bottom thereof through which said hook-like clamping teeth and said abutment faces of said clamping tongues of said protective sleeve extend; (c) edges at said apertures which form said retaining rim at said rear end of said barrel on which said clamping teeth engage; and (d) an opening at a rear side thereof through which said disc-shaped pusher member passes into said box-like head.

8. A safety syringe as claimed in claim 7 and further including a removable safety means for at least partly closing said opening provided at the rear side of said box-like head and for thereby preventing said pusher member from entering said box-like head.

9. A safety syringe as claimed in claim 8 wherein said safety means includes a tearable strip of paper material having a hole therein and a radial cut extending from said hole such that said stem passes through said hole and said tearable strip is positioned between said pusher member and said retaining rim of said box-like head.

10. A safety syringe as claimed in claim 8 wherein said safety means includes a cover member having a radial cut therein through which said stem passes and extensions which are fitted through said opening in the rear side of said box-like head to cooperate with said clamping tongues so as to prevent said clamping tongues from being flexed from engagement with said retaining rim.

11. A safety syringe as claimed in claim 1 wherein said rear end of said barrel includes at least one stop member against which said protective sleeve backwardly bears axially when in the retracted position; and wherein said protective sleeve includes at least two diametrically opposite tabs radially extending from a periphery thereof adjacent a rear end thereof whereby said tabs are engaged by two fingers of a user during movement of said plunger from the retracted position to the forwardmost position.

12. A safety syringe as claimed in claim 1 wherein said injection needle includes a needle carrying member which is disengagingly attached to the fore end of said barrel; and wherein said locking means locks said protective sleeve in the advanced position to said needle carrying member.

13. A safety syringe as claimed in claim 12 wherein said locking means includes (a) at least one locking inward projection provided in said protective sleeve, (b) a first outward projection provided on said needle carrying member which cooperates with said inward projection of said protective sleeve, (c) at least one locking tongue formed in said protective sleeve by a cut in said protective sleeve, said locking tongue extending longitudinally and having a forward end integral with said protective sleeve and a rear free end which tends to elastically flex radially inwardly, and (d) at least one second outward projection provided on said needle carrying member which cooperates with a respective said locking tongue; whereby when said protective sleeve is in the advanced safety position (a) said locking inward projection in said protective sleeve bears forwardly against said respective first outward projection in said needle carrying member and (b) each said rear free end of a respective said locking tongue bears backwardly against a respective said second outward projection of said needle carrying member.

14. A safety syringe as claimed in claim 12 wherein said protective sleeve includes a retaining inward projection and wherein said needle carrying member an outward projection against which said retaining inward projection of said protective sleeve bears when said sleeve is in the retracted rest position such that said protective sleeve thereby prevents said needle carrying member from being removed from the fore end of said barrel.

15. A safety syringe as claimed in claim 14 and further including a needle-covering cap having a rear end portion with an outside diameter which is disengagingly attached to a fore end of said needle-carrying member; and wherein a fore end of said protective sleeve is located close to said rear end portion of said cap when said protective sleeve is in the retracted rest position and wherein said protective sleeve includes a fore end part having a forward hole therein which is tapered relative to a remainder of an inside diameter of said protective sleeve and which is only slightly greater than said outside diameter of said rear end portion of said needle-covering cap.

16. A safety syringe as claimed in claim 15 wherein said protective sleeve further includes a tubular member secured unremovably to a remainder of said protective sleeve, said tubular member including said tapered forward hole and said retaining inward projection.

17. A safety syringe as claimed in claim 3 wherein said stem includes an easily broken weakened portion located between said pusher member and a knob at a rearmost end of said rear end section of said stem.

18. A safety syringe as claimed in claim 2 and further including a slip-back preventing means for preventing said stem from any backward displacement of said plunger once said plunger has been moved from the retracted position to the forwardmost position.

19. A safety syringe as claimed in claim 18 wherein said injection needle includes a needle carrying member which is disengagingly attached to the fore end of said barrel; and wherein said locking means locks said protective sleeve in the advanced position to said needle carrying member.

20. A safety syringe as claimed in claim 19 wherein said stem includes an easily broken weakened portion located adjacent a knob at a rearmost end of said rear end section of said stem.

* * * * *